(12) United States Patent
Lyon et al.

(10) Patent No.: US 12,193,718 B2
(45) Date of Patent: Jan. 14, 2025

(54) ORTHOPEDIC SURGICAL INSTRUMENT

(71) Applicants: Smith & Nephew, Inc., Memphis, TN (US); Smith & Nephew Orthopaedics AG, Zug (CH); Smith & Nephew Asia Pacific Pte. Limited, Singapore (SG)

(72) Inventors: Gregory A. Lyon, Fortville, IN (US); Robert Anderson Till, Jr., Avon, IN (US); John P. Hengesbach, Carmel, IN (US)

(73) Assignees: Smith & Nephew, Inc., Memphis, TN (US); Smith & Nephew Orthopaedics AG, Zug (CH); Smith & Nephew Asia Pacific Pte. Limited, Singapore (SG)

( * ) Notice: Subject to any disclaimer, the term of this patent is extended or adjusted under 35 U.S.C. 154(b) by 452 days.

(21) Appl. No.: 17/705,344

(22) Filed: Mar. 27, 2022

(65) Prior Publication Data

US 2022/0323134 A1    Oct. 13, 2022

Related U.S. Application Data

(60) Provisional application No. 63/173,091, filed on Apr. 9, 2021.

(51) Int. Cl.
*A61B 17/92* (2006.01)
*A61B 17/00* (2006.01)

(52) U.S. Cl.
CPC .... *A61B 17/92* (2013.01); *A61B 2017/00398* (2013.01); *A61B 2017/925* (2013.01); *A61B 2017/928* (2013.01)

(58) Field of Classification Search
CPC ............... A61B 17/92; A61B 17/1659; A61B 2017/922; A61B 2017/924; B25D 11/106;
(Continued)

(56) References Cited

U.S. PATENT DOCUMENTS 1,511,566 A * 10/1924 Kollock ............... B25D 11/102
74/567
1,578,275 A * 3/1926 Willi ................... B25D 11/102
74/56
(Continued)

FOREIGN PATENT DOCUMENTS

CN       101272739 A     9/2008
CN       101351161 A     1/2009
(Continued)

OTHER PUBLICATIONS

US 9,445,923 B2, 09/2016, Inventor (withdrawn)

*Primary Examiner* — David W Bates
(74) *Attorney, Agent, or Firm* — KDW Firm PLLC

(57) ABSTRACT

An orthopedic surgical instrument or impactor is disclosed. The surgical instrument being configured to provide a first forward energy or motion to drive a surgical tool (e.g., a broach, a rasp, a cutting tool, etc.) and/or an orthopedic implant (e.g., an intramedullary nail, a stem, etc.) into a patient's bone and a second reverse energy or motion to, for example, remove a stuck or lodged surgical tool or implant from a patient's bone. In one embodiment, the surgical instrument incorporates dual springs and dual masses (impactors) to store and release energy on demand to deliver an impact force in both forward and reverse directions. In one embodiment, the surgical instrument may also include a forward energy adjuster and a reverse energy adjuster so that a user can independently adjust the amount of energy provided in the forward and reverse directions as well as a means to adjust impact frequency.

19 Claims, 9 Drawing Sheets

(58) Field of Classification Search
CPC ........ B25D 2211/067; B25D 2211/064; B25D 11/102; B25D 11/068; Y10T 74/18304; A61F 2002/4681; A61F 2002/4619
See application file for complete search history.

(56) References Cited

U.S. PATENT DOCUMENTS

| | | | | |
|---|---|---|---|---|
| 1,609,494 | A | * | 12/1926 | Payne ............... B25D 11/106 173/100 |
| 1,777,875 | A | * | 10/1930 | Champayne ......... B25D 11/108 173/205 |
| 1,809,884 | A | * | 6/1931 | Anthony ............. B25D 11/102 173/132 |
| 1,825,072 | A | * | 9/1931 | Keller ............... B25D 11/102 74/56 |
| 2,655,921 | A | * | 10/1953 | Haboush ............ A61B 17/1604 81/463 |
| 2,713,992 | A | * | 7/1955 | Snyder .................. E21B 4/10 175/324 |
| 2,749,548 | A | * | 6/1956 | Turner ............... B25D 17/005 173/133 |
| 2,967,302 | A | * | 1/1961 | Loveless ............... H02K 33/14 173/133 |
| 3,149,681 | A | * | 9/1964 | Drew ................ B25D 17/005 173/203 |
| 3,430,707 | A | * | 3/1969 | Rees ................. B25D 11/106 173/48 |
| 4,428,439 | A | * | 1/1984 | Moreno ............... B25D 11/102 74/56 |
| 4,450,919 | A | * | 5/1984 | Cousineau ........... B25D 17/005 173/29 |
| 4,489,792 | A | * | 12/1984 | Fahim ................ B25D 11/106 173/29 |
| 5,057,112 | A | * | 10/1991 | Sherman ............ A61B 17/1659 606/86 R |
| 5,494,115 | A | * | 2/1996 | Hwong ............... B25D 16/006 173/13 |
| 6,138,772 | A | * | 10/2000 | Miescher ............ B25D 16/00 173/205 |
| 6,723,102 | B2 | | 4/2004 | Johnson et al. |
| 6,991,655 | B2 | | 1/2006 | Iversen |
| 7,189,241 | B2 | | 3/2007 | Yoon et al. |
| 7,594,933 | B2 | | 9/2009 | Kammerzell et al. |
| 7,604,637 | B2 | | 10/2009 | Johnson et al. |
| 7,634,306 | B2 | | 12/2009 | Sarin et al. |
| 7,636,595 | B2 | | 12/2009 | Marquart et al. |
| 7,780,681 | B2 | | 8/2010 | Sarin et al. |
| 7,927,338 | B2 | | 4/2011 | Laffargue et al. |
| 8,007,448 | B2 | | 8/2011 | Moctezuma de La Barrera |
| 8,206,405 | B2 | | 6/2012 | Beverland et al. |
| 8,394,036 | B2 | | 3/2013 | Kozak |
| 8,449,551 | B2 | | 5/2013 | Amiot et al. |
| 8,494,825 | B2 | | 7/2013 | Thornberry |
| 8,602,124 | B2 | | 12/2013 | Pedicini |
| 8,709,016 | B2 | | 4/2014 | Park et al. |
| 8,731,253 | B2 | | 5/2014 | Dardenne et al. |
| 8,790,351 | B2 | | 7/2014 | Paradis et al. |
| 8,814,877 | B2 | | 8/2014 | Wasielewski |
| 8,828,008 | B2 | | 9/2014 | Stubbs |
| 8,861,818 | B2 | | 10/2014 | Ito et al. |
| 8,936,106 | B2 | | 1/2015 | Pedicini |
| 8,974,468 | B2 | | 3/2015 | Borja |
| 8,979,859 | B2 | | 3/2015 | Leparmentier et al. |
| 9,005,213 | B2 | | 4/2015 | Fortin et al. |
| 9,011,456 | B2 | | 4/2015 | Ranawat et al. |
| 9,017,335 | B2 | | 4/2015 | Stiehl |
| 9,044,345 | B2 | | 6/2015 | Warkentine et al. |
| 9,095,375 | B2 | | 8/2015 | Haimerl et al. |
| 9,168,153 | B2 | | 10/2015 | Bettenga |
| 9,168,154 | B2 | | 10/2015 | Behzadi |
| 9,220,572 | B2 | | 12/2015 | Meridew et al. |
| 9,220,612 | B2 | | 12/2015 | Behzadi |
| 9,248,002 | B2 | | 2/2016 | McCarthy |
| 9,308,005 | B2 | | 4/2016 | Fitz et al. |
| 9,375,222 | B2 | | 6/2016 | Fitz et al. |
| 9,402,727 | B2 | | 8/2016 | Stubbs |
| 9,408,617 | B2 | | 8/2016 | Ranawat et al. |
| 9,469,160 | B2 | | 10/2016 | Koshio |
| 9,532,730 | B2 | | 1/2017 | Wasielewski |
| 9,539,112 | B2 | | 1/2017 | Thornberry |
| 9,554,863 | B2 | | 1/2017 | Paradis et al. |
| 9,572,682 | B2 | | 2/2017 | Aghazadeh |
| 9,585,768 | B2 | | 3/2017 | Sherman et al. |
| 9,649,160 | B2 | | 5/2017 | van der Walt et al. |
| 9,649,201 | B2 | | 5/2017 | Stuchin |
| 9,649,202 | B2 | | 5/2017 | Behzadi et al. |
| 9,662,228 | B2 | | 5/2017 | McCarthy |
| 9,713,506 | B2 | | 7/2017 | Fanson et al. |
| 9,713,539 | B2 | | 7/2017 | Haimerl et al. |
| 9,763,738 | B2 | | 9/2017 | Paradis et al. |
| 9,827,112 | B2 | | 11/2017 | Bettenga |
| 9,931,059 | B2 | | 4/2018 | Borja |
| 9,949,797 | B2 | | 4/2018 | Meridew et al. |
| 9,980,780 | B2 | | 5/2018 | Lang |
| 9,987,148 | B2 | | 6/2018 | Li et al. |
| RE46,954 | E | | 7/2018 | Pedicini |
| RE46,979 | E | | 8/2018 | Pedicini |
| 10,159,530 | B2 | | 12/2018 | Lang |
| 10,166,083 | B2 | | 1/2019 | Paradis et al. |
| 10,172,722 | B2 | | 1/2019 | Behzadi et al. |
| 10,245,162 | B2 | | 4/2019 | Behzadi et al. |
| 10,271,963 | B2 | | 4/2019 | Lye |
| 10,321,852 | B2 | | 6/2019 | Borja |
| 10,342,591 | B2 | | 7/2019 | Pedicini |
| 10,363,149 | B2 | | 7/2019 | van der Walt et al. |
| 10,405,928 | B2 | | 9/2019 | Falardeau et al. |
| 10,413,425 | B2 | | 9/2019 | Behzadi et al. |
| 10,420,567 | B2 | | 9/2019 | Pedicini |
| 10,426,540 | B2 | | 10/2019 | Behzadi |
| 10,441,244 | B2 | | 10/2019 | Behzadi |
| 10,456,271 | B2 | | 10/2019 | Behzadi |
| 10,463,415 | B2 | | 11/2019 | Walter et al. |
| 10,463,505 | B2 | | 11/2019 | Behzadi |
| 10,463,507 | B2 | | 11/2019 | Nic |
| 10,470,897 | B2 | | 11/2019 | Behzadi |
| 10,478,318 | B2 | | 11/2019 | Behzadi et al. |
| 10,568,643 | B2 | | 2/2020 | Johnson et al. |
| 10,603,115 | B2 | | 3/2020 | van der Walt et al. |
| 10,716,630 | B2 | | 7/2020 | Krebs et al. |
| 10,743,950 | B2 | | 8/2020 | Nikou et al. |
| 10,881,470 | B2 | | 1/2021 | Falardeau et al. |
| 10,912,597 | B2 | | 2/2021 | Pedicini |
| 10,918,499 | B2 | | 2/2021 | Nielsen et al. |
| 10,980,645 | B2 | | 4/2021 | Falardeau et al. |
| 11,020,245 | B2 | | 6/2021 | van der Walt et al. |
| 11,033,315 | B2 | | 6/2021 | Pedicini |
| 11,090,170 | B2 | | 8/2021 | Li et al. |
| 11,103,363 | B2 | | 8/2021 | Bettenga |
| 11,147,638 | B2 | | 10/2021 | Nikou et al. |
| 11,179,062 | B2 | | 11/2021 | Borja |
| 11,213,336 | B2 | | 1/2022 | Walter et al. |
| 11,229,491 | B2 | | 1/2022 | Nikou et al. |
| 11,234,775 | B2 | | 2/2022 | Shiels et al. |
| 11,284,951 | B2 | | 3/2022 | Nikou et al. |
| 2004/0087852 | A1 | | 5/2004 | Chen et al. |
| 2004/0147926 | A1 | | 7/2004 | Iversen |
| 2004/0206525 | A1 | * | 10/2004 | Rask ................. B25D 11/102 173/205 |
| 2005/0065617 | A1 | | 3/2005 | Moctezuma de la Barrera et al. |
| 2005/0148855 | A1 | | 7/2005 | Kienzle |
| 2005/0187562 | A1 | | 8/2005 | Grimm et al. |
| 2006/0064109 | A1 | | 3/2006 | Iversen |
| 2006/0094958 | A1 | | 5/2006 | Marquart et al. |
| 2006/0190011 | A1 | | 8/2006 | Ries |
| 2007/0225725 | A1 | | 9/2007 | Heavener et al. |
| 2008/0269596 | A1 | | 10/2008 | Revie et al. |
| 2010/0076505 | A1 | | 3/2010 | Borja |
| 2010/0137871 | A1 | | 6/2010 | Borja |
| 2010/0261998 | A1 | | 10/2010 | Stiehl |
| 2010/0274253 | A1 | | 10/2010 | Ure |
| 2011/0190775 | A1 | | 8/2011 | Ure |
| 2012/0209117 | A1 | | 8/2012 | Mozes et al. |
| 2012/0209419 | A1 | | 8/2012 | Kang et al. |

(56) References Cited

U.S. PATENT DOCUMENTS

| | | |
|---|---|---|
| 2012/0283599 A1 | 11/2012 | Borja |
| 2012/0323247 A1 | 12/2012 | Bettenga |
| 2013/0172907 A1 | 7/2013 | Harris |
| 2013/0261681 A1* | 10/2013 | Bittenson .............. A61B 17/92 606/86 R |
| 2014/0052149 A1 | 2/2014 | van der Walt et al. |
| 2014/0135773 A1 | 5/2014 | Stein et al. |
| 2014/0135791 A1 | 5/2014 | Nikou et al. |
| 2014/0303631 A1 | 10/2014 | Thornberry |
| 2014/0364848 A1 | 12/2014 | Heimbecher et al. |
| 2015/0142372 A1 | 5/2015 | Singh |
| 2015/0143372 A1 | 5/2015 | Bercovici et al. |
| 2015/0150692 A1 | 6/2015 | Lye |
| 2015/0182351 A1 | 7/2015 | Behzadi |
| 2015/0272478 A1 | 10/2015 | Borja |
| 2016/0038307 A1 | 2/2016 | Bettenga |
| 2016/0100958 A1 | 4/2016 | Behzadi et al. |
| 2016/0135900 A1 | 5/2016 | Falardeau et al. |
| 2016/0157751 A1 | 6/2016 | Mahfouz |
| 2016/0199199 A1* | 7/2016 | Pedicini .............. A61B 17/92 606/100 |
| 2016/0220315 A1 | 8/2016 | Falardeau et al. |
| 2016/0220318 A1 | 8/2016 | Falardeau et al. |
| 2016/0220385 A1 | 8/2016 | Falardeau et al. |
| 2016/0242934 A1 | 8/2016 | van der Walt et al. |
| 2016/0249968 A1 | 9/2016 | Walter et al. |
| 2017/0065429 A1 | 3/2017 | Behzadi et al. |
| 2017/0065430 A1 | 3/2017 | Singh |
| 2017/0065431 A1 | 3/2017 | Singh |
| 2017/0065432 A1 | 3/2017 | Singh |
| 2017/0119475 A1 | 5/2017 | McCabe et al. |
| 2017/0172697 A1 | 6/2017 | Aghazadeh |
| 2017/0172762 A1 | 6/2017 | Sherman et al. |
| 2017/0196506 A1 | 7/2017 | Behzadi |
| 2017/0196701 A1 | 7/2017 | Behzadi et al. |
| 2017/0196704 A1 | 7/2017 | Behzadi et al. |
| 2017/0196705 A1 | 7/2017 | Behzadi |
| 2017/0196706 A1 | 7/2017 | Behzadi |
| 2017/0196707 A1 | 7/2017 | Behzadi |
| 2017/0196708 A1 | 7/2017 | Behzadi et al. |
| 2017/0196710 A1 | 7/2017 | Behzadi |
| 2017/0196711 A1 | 7/2017 | Behzadi |
| 2017/0202682 A1 | 7/2017 | McCarthy |
| 2017/0202683 A1 | 7/2017 | Behzadi |
| 2017/0296274 A1 | 10/2017 | van der Walt et al. |
| 2017/0340456 A1 | 11/2017 | Behzadi |
| 2017/0348059 A1 | 12/2017 | Kang et al. |
| 2017/0354368 A1 | 12/2017 | Behzadi |
| 2017/0360575 A1 | 12/2017 | Behzadi et al. |
| 2018/0049622 A1 | 2/2018 | Ryan et al. |
| 2018/0055518 A1* | 3/2018 | Pedicini .............. A61B 17/17 |
| 2018/0055553 A1* | 3/2018 | Pedicini .............. B25D 11/066 |
| 2018/0055554 A1* | 3/2018 | Pedicini .............. B25D 11/066 |
| 2018/0078201 A1 | 3/2018 | Behzadi |
| 2018/0078388 A1 | 3/2018 | Bettenga |
| 2018/0092757 A1 | 4/2018 | Behzadi et al. |
| 2018/0125474 A1* | 5/2018 | Dougherty ....... A61B 17/00234 |
| 2018/0168740 A1 | 6/2018 | Ryan et al. |
| 2018/0185107 A1 | 7/2018 | Nikou et al. |
| 2018/0193171 A1 | 7/2018 | van der Walt et al. |
| 2018/0250144 A1 | 9/2018 | Li et al. |
| 2018/0263704 A1 | 9/2018 | Lang |
| 2018/0271601 A1 | 9/2018 | Meridew et al. |
| 2018/0296365 A1 | 10/2018 | Nielsen et al. |
| 2018/0303379 A1 | 10/2018 | Borja |
| 2018/0303564 A1 | 10/2018 | Nikou et al. |
| 2018/0318017 A1 | 11/2018 | Fanson et al. |
| 2018/0333275 A1 | 11/2018 | Behzadi et al. |
| 2018/0338751 A1* | 11/2018 | Pedicini .............. A61F 2/4603 |
| 2018/0338799 A1 | 11/2018 | Hladio et al. |
| 2018/0344414 A1 | 12/2018 | Nikou et al. |
| 2019/0125293 A1 | 5/2019 | Behzadi |
| 2019/0133547 A1 | 5/2019 | Behzadi |
| 2019/0133700 A1 | 5/2019 | Nikou et al. |
| 2019/0133701 A1 | 5/2019 | Nikou et al. |
| 2019/0175291 A1 | 6/2019 | Hagag et al. |
| 2019/0182555 A1 | 6/2019 | Olson et al. |
| 2019/0183554 A1 | 6/2019 | Pedicini |
| 2019/0183555 A1* | 6/2019 | Pedicini .............. B25D 11/108 |
| 2019/0216521 A1* | 7/2019 | Chhatrala .......... A61B 17/921 |
| 2019/0223889 A1* | 7/2019 | Pedicini .............. A61B 17/1659 |
| 2019/0231446 A1 | 8/2019 | Bowling et al. |
| 2019/0282286 A1 | 9/2019 | Pedicini |
| 2019/0290449 A1 | 9/2019 | Wu et al. |
| 2019/0343548 A1 | 11/2019 | Behzadi |
| 2019/0350724 A1 | 11/2019 | Behzadi |
| 2019/0350725 A1 | 11/2019 | Behzadi |
| 2019/0350726 A1 | 11/2019 | Behzadi |
| 2019/0350727 A1 | 11/2019 | Behzadi |
| 2019/0350728 A1 | 11/2019 | van der Walt et al. |
| 2019/0357809 A1 | 11/2019 | Borja |
| 2019/0357958 A1 | 11/2019 | Walter et al. |
| 2020/0008774 A1 | 1/2020 | Behzadi |
| 2020/0015983 A1 | 1/2020 | Behzadi |
| 2020/0015984 A1 | 1/2020 | Behzadi |
| 2020/0022744 A1 | 1/2020 | Behzadi |
| 2020/0030117 A1 | 1/2020 | Nic |
| 2020/0046519 A1 | 2/2020 | Lim |
| 2020/0069279 A1 | 3/2020 | Behzadi et al. |
| 2020/0069280 A1 | 3/2020 | Behzadi et al. |
| 2020/0069438 A1 | 3/2020 | Singh |
| 2020/0155246 A1 | 5/2020 | Nikou et al. |
| 2020/0155247 A1 | 5/2020 | Nikou et al. |
| 2020/0268454 A1 | 8/2020 | Walter et al. |
| 2020/0294423 A1 | 9/2020 | Blain et al. |
| 2020/0352654 A1 | 11/2020 | van der Walt et al. |
| 2021/0093401 A1 | 4/2021 | Falardeau et al. |
| 2021/0220152 A1 | 7/2021 | Nielsen et al. |
| 2021/0228252 A1 | 7/2021 | Pedicini |
| 2021/0259854 A1 | 8/2021 | Falardeau et al. |
| 2021/0315716 A1 | 10/2021 | van der Walt et al. |
| 2021/0361336 A1 | 11/2021 | Adekanmbi et al. |
| 2022/0071509 A1 | 3/2022 | Borja |
| 2022/0142693 A1* | 5/2022 | Slocum .............. A61B 17/92 |
| 2022/0183735 A1* | 6/2022 | Wallace ............. A61F 2/4603 |
| 2022/0226033 A1* | 7/2022 | Slocum .............. A61F 2/4603 |
| 2022/0240947 A1* | 8/2022 | Marinkovich ..... A61B 17/1604 |
| 2022/0273317 A1* | 9/2022 | Levy .................. A61B 17/1659 |
| 2022/0313337 A1* | 10/2022 | Pedicini ............. A61B 17/1668 |
| 2023/0285062 A1* | 9/2023 | Santos ............... A61B 17/1628 |
| 2024/0024012 A1* | 1/2024 | Dittrich ............. A61B 17/1624 |

FOREIGN PATENT DOCUMENTS

| | | |
|---|---|---|
| CN | 201422925 Y | 3/2010 |
| CN | 101889897 A | 11/2010 |
| WO | 03068078 A1 | 8/2003 |
| WO | 2008017648 A1 | 2/2008 |
| WO | 2013169334 A1 | 11/2013 |
| WO | 2017123506 A1 | 7/2017 |
| WO | 2018031752 A1 | 2/2018 |
| WO | 2018128765 A1 | 7/2018 |

* cited by examiner

ORTHOPEDIC SURGICAL INSTRUMENT

CROSS-REFERENCE TO RELATED APPLICATIONS

This is a non-provisional of, and claims the benefit of the filing date of, U.S. provisional patent application No. 63/173,091, filed Apr. 9, 2021, entitled "Orthopedic Surgical Instrument," the entirety of which application is incorporated by reference herein.

TECHNICAL FIELD

The present disclosure is directed to an orthopedic surgical instrument, and more specifically to an orthopedic surgical instrument or impactor arranged and configured to transmit a first forward energy or motion to, for example, drive a surgical tool (e.g., a broach) or implant into a patient's bone, and a second reverse energy or motion to, for example, remove a stuck or lodged surgical tool (e.g., a broach) or implant from a patient's bone.

BACKGROUND

Orthopedic surgical procedures such as, for example, hip procedures, knee procedures, shoulder procedures, etc., have become common place in today's society. For example, total hip arthroplasty or hip replacement is a well-known procedure for repairing damaged bone (e.g., a damaged hip). During a total hip arthroplasty, an acetabular system may be implanted into a patient's acetabulum. In addition, and/or alternatively, a femoral implant may be implanted into a patient's femur. During the surgical procedure, the patient's bone typically needs to be prepared to receive the surgical implant. For example, an orthopedic tool such as, for example, an orthopedic broach, rasp, cutting tool, etc. (terms used interchangeably herein without the intent to limit) may be used to prepare an inner surface of a patient's intramedullary canal to receive an orthopedic implant such as, for example, a femoral hip prosthesis, an intramedullary nail, etc. The preparation of the intramedullary canal by the surgeon is designed to insure a proper fit between the patient's femur and the implant. In addition, during removal of the broach from the patient's intramedullary canal, the broach may become stuck within the patient's intramedullary canal.

With this in mind, various surgical tools have been developed to assist surgeons during orthopaedic procedures to place and/or remove various objects. For example, mallets are frequently used to apply an impacting force on the orthopedic tool (e.g., broach) to remove bones or other implanted objects. In addition, mallets may be used to assist in removing the orthopedic tool (e.g., broach) if it becomes stuck during the surgical procedure. Moreover, mallets may also be used to assist the surgeon with inserting the implant. While mallets are effective, the impacting force must be axially applied to avoid mishitting and/or misalignment of the implant or the inadvertent removal of the patient's bone. Moreover, the force applied should be sufficiently controlled to avoid unwanted damage to the patient's bone.

As a result, orthopedic impactors or slap hammers (terms used interchangeably herein without the intent to limit) have been developed to assist with driving a surgical tool or implant into the patient's bone, and to remove a stuck or lodged surgical tool or implant from the patient's bone.

However, most orthopedic impactors still have several drawbacks. For example, orthopedic impactors may be large, heavy, and bulky, thus difficult to handle.

Accordingly, there remains a need for an improved orthopedic impactor. It is with this in mind that the present disclosure is provided.

SUMMARY

This Summary is provided to introduce a selection of concepts in a simplified form that are further described below in the Detailed Description. This Summary is not intended to identify key features or essential features of the claimed subject matter, nor is it intended as an aid in determining the scope of the claimed subject matter.

Disclosed herein is an orthopedic surgical instrument arranged and configured to provide a first forward energy or motion to drive a surgical tool (e.g., a broach, a rasp, a cutting tool, etc.) and/or an orthopedic implant (e.g., an intramedullary nail, a stem, etc.) into a patient's bone. In addition, the orthopedic surgical instrument may be reversed to provide a second reverse energy or motion to, for example, remove a stuck or lodged surgical tool or implant from a patient's bone.

In one embodiment, the orthopedic surgical instrument includes a launch cog assembly arranged and configured to interact with a motor such that activation of the motor moves (e.g., rotates) the launch cog assembly in a desired direction. Depending on the desired direction of operation of the orthopedic surgical instrument (e.g., forward or reverse), rotation of the launch cog assembly causes the launch cog assembly to interact with one of a forward impactor or a reverse impactor, which causes the impactor to compress a respective impaction spring until associated ramped surfaces formed on the launch cog assembly and the engaged impactor disengage, at which point the compressed spring bias the impactor forward or backwards into engagement with an impaction shaft causing the energy to be transferred to the surgical tool or implant coupled to the orthopedic surgical instrument.

As such, in one embodiment, the orthopedic surgical instrument incorporates dual springs and dual masses (impactors) to store and release energy on demand to deliver an impact force in both forward and reverse directions.

In one embodiment, the orthopedic surgical instrument may also include an energy adjuster arranged and configured to adjust the energy or impact force provided by the orthopedic surgical instrument. In one embodiment, the orthopedic surgical instrument may include a forward energy adjuster and a reverse energy adjuster so that a user can independently adjust the amount of energy provided in the forward direction and in the reverse direction.

In one embodiment, an orthopedic surgical instrument is disclosed. In use, the orthopedic surgical instrument is arranged and configured to deliver a first forward motion to drive a surgical tool or implant into a patient's bone and a second reverse motion to remove a surgical tool or implant from the patient's bone.

In one embodiment, the surgical instrument includes a housing, a motor positioned within the housing, a launch cog assembly, a forward impactor, and a reverse impactor. The motor includes a first gear. The launch cog assembly includes a second gear arranged and configured to interact with the first gear of the motor so that activation of the motor rotates the launch cog assembly in one of a first direction or a second direction. The log cog assembly includes a first end and a second end. The forward impactor is arranged and configured to interact with the first end of the launch cog assembly. The reverse impactor is arranged and configured to interact with the second end of the launch cog assembly. In use, with the orthopedic surgical instrument in a forward configuration, activation of the motor rotates the launch cog assembly in the first direction causing the first end of the launch cog assembly to interact with the forward impactor to axially translate the forward impactor. In use, with the orthopedic surgical instrument in a reverse configuration, activation of the motor rotates the launch cog assembly in the second direction causing the second end of the launch cog assembly to interact with the reverse impactor to axially translate the reverse impactor.

In one embodiment, the first end of the launch cog assembly includes a first ramped surface, the second end of the launch cog assembly includes a second ramped surface, the forward impactor includes a ramped surface arranged and configured to interact with the first ramped surface of the launch cog assembly, and the reverse impactor includes a ramped surface arranged and configured to interact with the second ramped surface of the launch cog assembly.

In one embodiment, the orthopedic surgical instrument further includes a shaft, the launch cog assembly, the forward impactor, and the reverse impactor being mounted about the shaft.

In one embodiment, the orthopedic surgical instrument further includes a first spring and a second spring. The first spring being positioned about the shaft, the first spring positioned between the forward impactor and a first shoulder of the shaft. The second spring being positioned about the shaft, the second spring positioned between the reverse impactor and a second shoulder of the shaft.

In one embodiment, with the orthopedic surgical instrument in the forward configuration, interaction between the first ramped surface on the first end of the launch cog assembly and the ramped surface on the forward impactor causes the first spring to compress until the first ramped surface on the first end of the launch cog assembly and the ramped surface on the forward impactor disengage causing the first spring to axially drive the forward impactor relative to the shaft.

In one embodiment, with the orthopedic surgical instrument in the reverse configuration, interaction between the second ramped surface on the second end of the launch cog assembly and the ramped surface on the reverse impactor causes the second spring to compress until the second ramped surface on the second end of the launch cog assembly and the ramped surface on the reverse impactor disengage causing the second spring to axially drive the reverse impactor relative to the shaft.

In one embodiment, with the orthopedic surgical instrument in the forward configuration, the forward impactor is rotationally stationary relative to the shaft.

In one embodiment, with the orthopedic surgical instrument in the forward configuration, the reverse impactor is rotatable relative to the shaft so that the reverse impactor rotates with the launch cog assembly.

In one embodiment, with the orthopedic surgical instrument in the reverse configuration, the reverse impactor is rotationally stationary relative to the shaft, and the forward impactor is rotatable relative to the shaft so that the forward impactor rotates with the launch cog assembly.

In one embodiment, the orthopedic surgical instrument further includes a forward impactor anti-rotational sleeve and a reverse impactor anti-rotational sleeve. The forward impactor anti-rotational sleeve includes an internal bore arranged and configured to receive the forward impactor therein and a pawl arranged and configured to selectively engage the forward impactor depending on a direction of rotation, engagement of the pawl with the forward impactor prevents relative rotation of the forward impactor. The reverse impactor anti-rotational sleeve includes an internal bore arranged and configured to receive the reverse impactor therein and a pawl arranged and configured to selectively engage the reverse impactor depending on the direction of rotation, engagement of the pawl with the reverse impactor prevents relative rotation of the reverse impactor.

In one embodiment, the orthopedic surgical instrument further includes a forward energy adjuster and a reverse energy adjuster arranged and configured to enable a user to independently adjust an amount of energy provided in the forward configuration and in the reverse configuration.

In one embodiment, the forward energy adjuster includes a first knob including an internal thread arranged and configured to engage a corresponding thread operatively associated with the first shoulder of the shaft, in use, rotation of the first knob in a first direction compresses the first spring to increase a preload on the first spring, rotation of the first knob in a second direction relaxes the first spring to decrease the preload on the first spring. The reverse energy adjuster includes a second knob including an internal thread arranged and configured to engage a corresponding thread operatively associated with the second shoulder of the shaft, in use, rotation of the second knob in a first direction compresses the second spring to increase a preload on the second spring, rotation of the second knob in a second direction relaxes the second spring to decrease the preload on the second spring.

In one embodiment, the orthopedic surgical instrument further includes a selector mechanism arranged and configured to transition the orthopedic surgical instrument between forward configuration and the reverse configuration.

In one embodiment, the orthopedic surgical instrument further includes a coupling mechanism operatively associated with the shaft, the coupling mechanism arranged and configured to couple to a surgical tool or an implant.

Embodiments of the present disclosure provide numerous advantages. For example, the orthopedic surgical instrument enables a surgeon to accurately and safely apply a force to a surgical implant or tool. For example, the orthopedic surgical instrument may be arranged and configured to apply a force to a broach used to prepare an intramedullary canal of a patient's bone and/or to assist with removal of the broach from the intramedullary canal of the patient's bone. The orthopedic surgical instrument is arranged and configured to apply a force to the broach, while minimizing the risk of injury to the patient or to the surgeon's hands during use. Moreover, in one embodiment, the orthopedic surgical instrument may be arranged and configured to enable the surgeon to separately and independently adjust the force applied by the orthopedic surgical instrument in the forward direction and the reverse direction so that, for example, a larger force may be applied in the reverse direction as compared to the forward direction.

Further features and advantages of at least some of the embodiments of the present invention, as well as the structure and operation of various embodiments of the present invention, are described in detail below with reference to the accompanying drawings.

BRIEF DESCRIPTION OF THE DRAWINGS

By way of example, a specific embodiment of the disclosed device will now be described, with reference to the accompanying drawings, in which.

Figure 1:
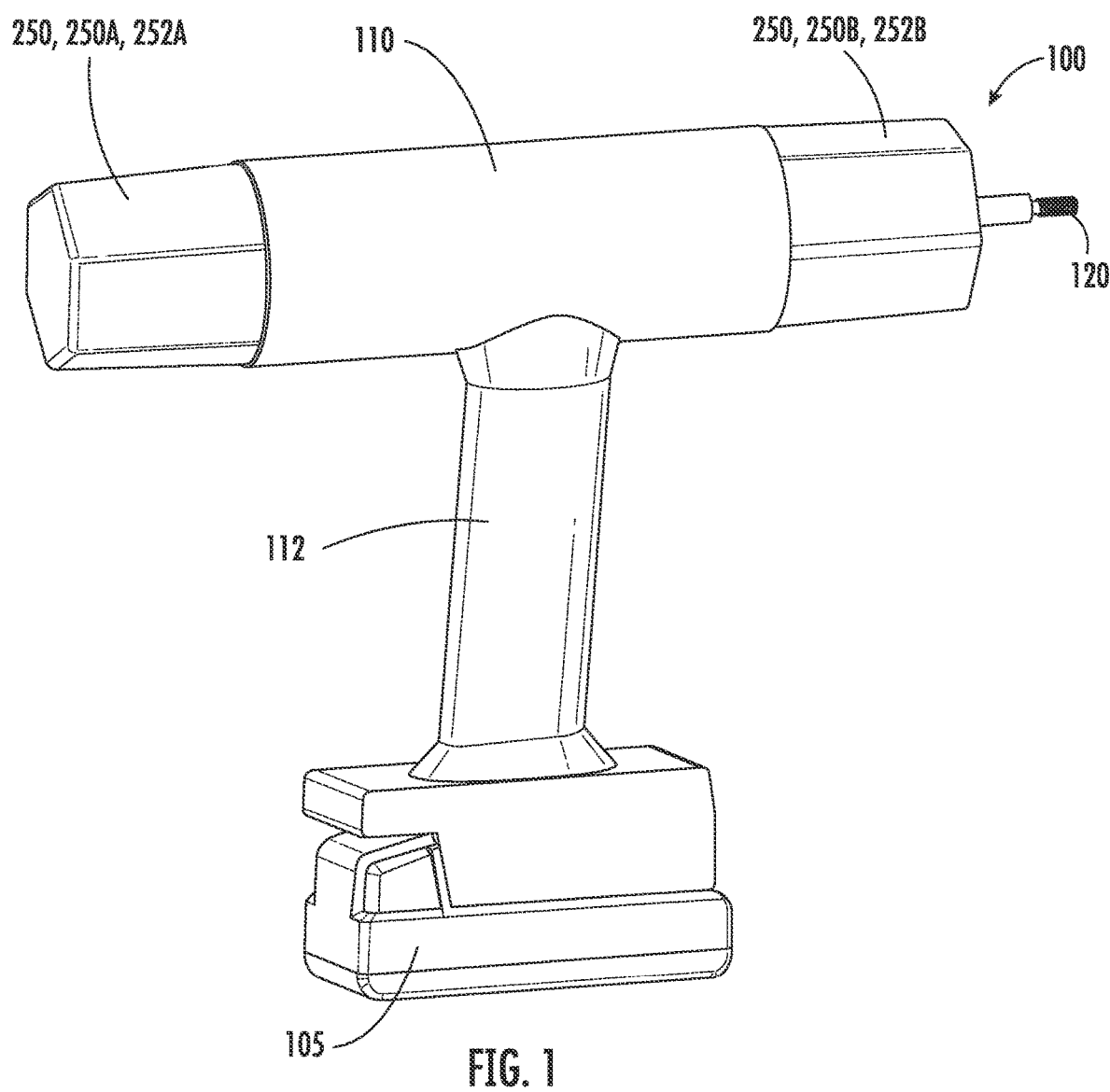
FIG. 1 illustrates a perspective view of an example embodiment of an orthopedic surgical instrument or impactor in accordance with one or more features of the present disclosure.

It should be understood that the drawings are not necessarily to scale and that the disclosed embodiments are sometimes illustrated diagrammatically and in partial views. In certain instances, details which are not necessary for an understanding of the disclosed methods and devices or which render other details difficult to perceive may have been omitted. It should be further understood that this disclosure is not limited to the particular embodiments illustrated herein. In the drawings, like numbers refer to like elements throughout unless otherwise noted.

DETAILED DESCRIPTION

Various features or the like of an orthopedic surgical instrument or impactor (terms used interchangeably herein without the intent to limit) arranged and configured to transmit a first forward energy or motion to, for example, drive a surgical tool (e.g., a broach) or implant into a patient's bone, and a second reverse energy or motion to, for example, remove a stuck or lodged surgical tool (e.g., a broach) or implant from a patient's bone will now be described more fully hereinafter with reference to the accompanying drawings, in which one or more features of the orthopedic impactor will be shown and described. It should be appreciated that the various features may be used independently of, or in combination, with each other. It will be appreciated that an orthopedic impactor as disclosed herein may be embodied in many different forms and should not be construed as being limited to the embodiments set forth herein. Rather, these embodiments are provided so that this disclosure will convey certain features of the orthopedic impactor to those skilled in the art.

As will be described herein, in accordance with one or more features of the present disclosure, the orthopedic impactor is arranged and configured to provide a first forward energy or motion to drive a surgical tool such as, for example, a broach, a rasp, a cutting tool, or an orthopedic implant such as, for example, an intramedullary nail, a stem, etc. into a patient's bone. In addition, the orthopedic impactor may be reversed to provide a second reverse energy or motion to, for example, remove a stuck or lodged surgical tool or implant from a patient's bone. It should be appreciated that while, for example, the orthopedic impactor may be described herein in connection with driving a broach into a patient's bone to, for example, prepare an intramedullary canal of the patient's bone, the present disclosure is not so limited and the orthopedic impactor may be used in connection with any surgical tool or implant now known or hereafter developed. As such, the present disclosure should not be limited to any particular surgical tool, implant, or procedure unless explicitly claimed.

In accordance with one or more features of the present disclosure, the orthopedic impactor is arranged and configured to accurately and safely apply a force to a surgical implant or tool, in particular a broach to prepare an intramedullary canal of a patient's bone and/or to assist with removal of the broach from the intramedullary canal of the patient's bone. The orthopedic impactor is arranged and configured to apply a force to the broach, while minimizing the risk of injury to the patient or to the surgeon's hands during use.

That is, in accordance with one or more features of the present disclosure, the orthopedic impactor helps the surgeon to deliver a force towards or away from a surgical area in a joint replacement procedure. For example, the orthopedic impactor is arranged and configured to provide a forward force to drive a surgical implant or tool such as a broach to prepare an intramedullary canal of a patient's bone or to deliver a reverse force to assist a surgeon in removing a surgical implant or tool from a patient's bone.

Referring to FIGS. 1-8, an example of an embodiment of motor-driven orthopedic impactor 100 will now be shown and described. As shown, the orthopedic impactor 100 may include battery 105 so that the orthopedic impactor 100 is configured to be battery-powered as will be readily appreciated by one of ordinary skill in the art. Thus arranged, the orthopedic impactor 100 may provide wireless portability. As will be appreciated however, the orthopedic impactor 100 may include any suitable motor and/or energy source (e.g., the orthopedic impactor 100 may be powered via AC power supplied through an electrical plug, etc.) now known or hereafter developed.

In use, as will be described in greater detail below, the orthopedic impactor 100 utilizes dual masses (e.g., forward and reverse impactors 180, 190) along with dual springs (e.g., forward and reverse impaction springs 184, 194) to store and release energy as needed. In use, the springs (e.g., forward and reverse impaction springs 184, 194) and masses (e.g., forward and reverse impactors 180, 190) are utilized to deliver an impact force in forward and reverse directions, respectively. For example, as will be described in greater detail below, the orthopedic impactor 100 may utilize a motor 130 to rotate a launch cog assembly 160, which rotationally interfaces with one of the forward and reverse impactors 180, 190 depending on the position of the selector, which in turn causes the impactor 180, 190 to compress its respective spring 184, 194 until interacting ramps 164, 166, 182, 192 formed on the launch cog assembly 160 and impactor 180, 190 disengage causing the compressed spring 184, 194 to expand and propel, drive, etc. the impactor 180, 190 causing the impactor 180, 190 to strike an impaction shaft or hammer rod 150, which transfers the impact energy to the attached surgical implant or tool. That is, as will be described in greater detail below, depending on the setting of the orthopedic impactor 100 (e.g., forward or reverse), activation of the motor 130 causes the launch cog assembly 160 to translate in one direction or the other, thereby causing the launch cog assembly 160 to interact with one or the other of the forward and reverse impactors 180, 190 until the impactor 180, 190 fires, striking the impaction shaft 150 and transferring the stored energy to the implant or tool coupled to the orthopedic impactor 100.

As described herein, the orthopedic impactor 100 may include the capabilities to perform single and multiple impacts, as well as impacting of variable and varying directions, forces, and frequencies. In some embodiments, the impact energy is adjustable. In certain embodiments, the impact is transferred to a surgical tool such as a broach, a chisel, a cutting tool, or other end effector connected to the orthopedic impactor 100.

Figure 2:
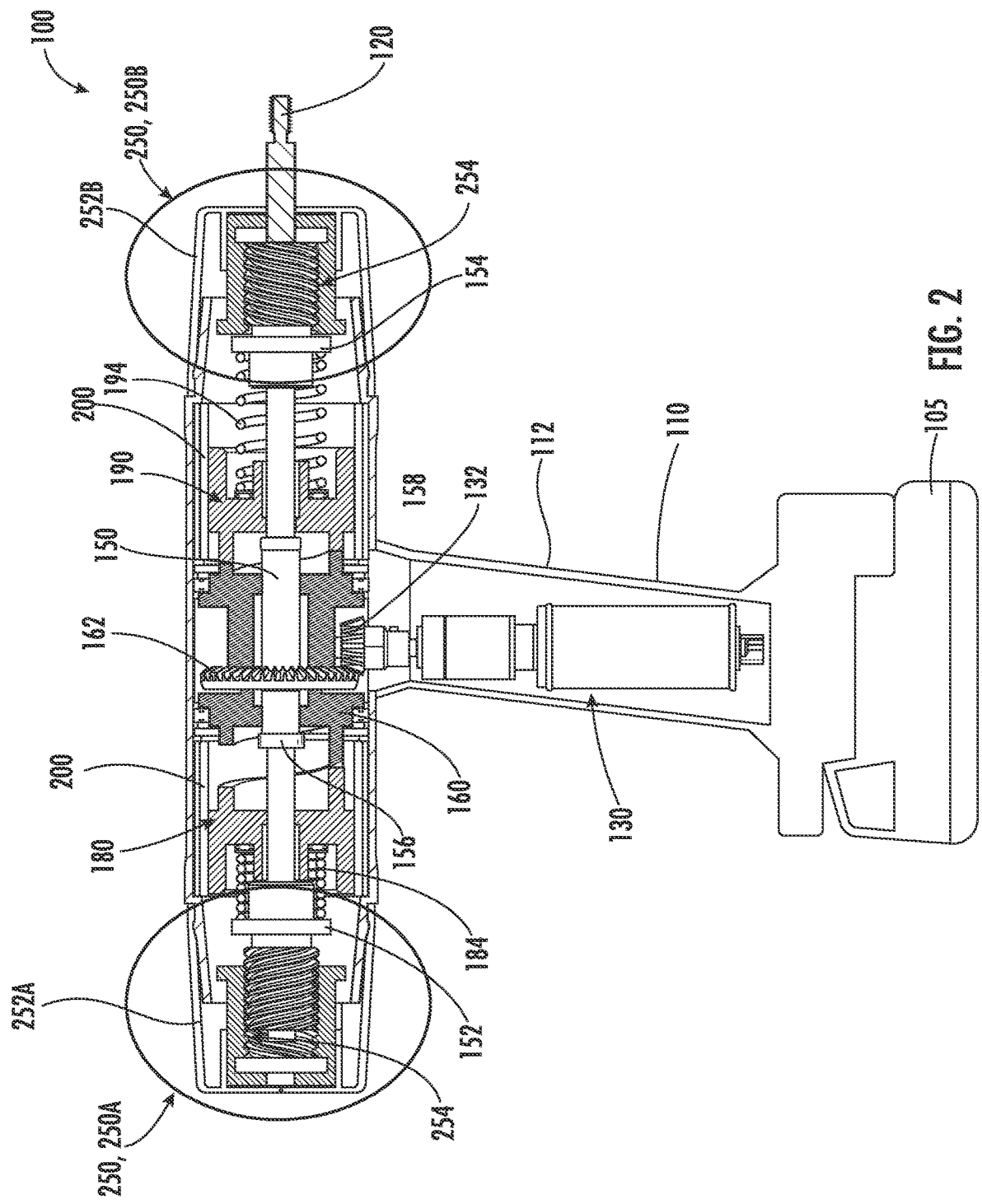
FIG. 2 illustrates a cross-sectional view of the orthopedic surgical instrument or impactor shown in FIG. 1, FIG. 2 shown with the housing removed to illustrate some of the internal components of the orthopedic surgical instrument or impactor.

Referring to FIGS. 1 and 2, the orthopedic impactor 100 includes a housing 110 arranged and configured to house one or more of the components of the orthopedic impactor 100. The housing 110 may be manufactured from any suitable material now known or hereafter developed such as, for example, a plastic or a metal. The housing 110 may also include a handle portion 112 with an optional hand grip for comfortable and secure holding of the orthopedic impactor 100. Alternatively, the housing 110 may incorporate a suitable mount interface for integrating the orthopedic impactor 100 into a robotic assembly while in use.

As illustrated, in one embodiment, the orthopedic impactor 100 may include a coupling mechanism 120 for coupling to an orthopedic implant or tool such as, for example, a broach, a chisel, a cutting tool, or other end effector known in the art. The coupling mechanism 120 may have a quick connect mechanism to facilitate rapid change.

Referring to FIG. 1, in one embodiment, the orthopedic impactor 100 includes a motor 130. As will be readily appreciated by one of ordinary skill in the art, the orthopedic impactor 100 also includes a trigger (not shown) for selectively activating the orthopedic impactor 100. In addition, the orthopedic impactor 100 includes a selector mechanism (not shown) such as, for example, a button, a slide, or the like to selectively move the orthopedic impactor 100 between a forward configuration or mode and a reverse configuration or mode. In one embodiment, moving the selector into the forward configuration causes the motor 130 to spin in a first direction while moving the selector into the reverse configuration causes the motor 130 to spin in a second, opposite direction. Thus arranged, in use, the motor 130 may be arranged and configured with motor direction control (e.g., motor 130 can spin in the clockwise and counter-clockwise direction depending on the position of the selector) to drive the orthopedic impactor 100 in the forward direction or the reverse direction. Alternatively, in one embodiment, moving the selector between the forward and reverse configurations causes the motor 130 to engage, for example, either forward or reverse levers to drive the orthopedic impactor 100 in the forward or reverse directions (e.g., lever engages either the forward impactor or the reverse impactor depending on the position of the selector).

As will be readily appreciated by one of ordinary skill in the art, incorporation of a trigger to activate the motor and/or a selector to transition the orthopedic impactor 100 between forward and reverse directions is well-known. Thus, for the sake of brevity, further discussion on operation and/or configuration of the trigger and selector are omitted herefrom.

Referring to FIG. 2, in one embodiment, the motor 130 is operatively coupled, either directly or indirectly, to a gear 132 such as, for example, a bevel gear so that rotation of the motor 130 causes the gear 132 to rotate, although incorporation of other forms of gears is readily envisioned.

As illustrated, the orthopedic impactor 100 includes a shaft, an impaction shaft, a hammer rod, etc. 150 (terms used interchangeably herein without the intent to limit) upon which various components of the orthopedic impactor 100 are mounted. In addition, referring to FIGS. 2-6, the orthopedic impactor 100 further includes a launch cog assembly 160. As illustrated, the launch cog assembly 160 includes a gear 162 such as, for example, a helical gear although other forms of gears are readily envisioned. The helical gear 162 is coupled to the bevel gear 132 associated with the motor 130 so that rotation of the motor 130 in the first (e.g., forward) direction rotates the launch cog assembly 160 in a first (e.g., clockwise) direction. Meanwhile, rotation of the motor 130 in the second (e.g., reverse) direction rotates the launch cog assembly 160 in a second (e.g., counter-clockwise) direction. In addition, the launch cog assembly 160 includes a first or forward end and a second or reverse end. As will be described in greater detail below, each of the first and second ends includes a ramped surface 164, 166 arranged and configured to interact with, contact, etc. a corresponding ramped surface 182, 192 formed on an end portion of a forward or reverse impactor 180, 190, respectively. That is, the orthopedic impactor 100 also includes a forward impactor 180 including a ramped surface 182 and a reverse impactor 190 including a ramped surface 192. Depending on whether the orthopedic impactor 100 is being driven in the forward or reverse direction, one or the ramped surfaces 164, 166 formed on one of the first or second ends of the launch cog assembly 160 interacts with one of the ramped surfaces 182, 192 of the forward or reverse impactors 180, 190. In addition, as illustrated, the orthopedic impactor 100 include a forward impaction spring 184 positioned between a first shoulder 152 associated with the impaction shaft 150 and the forward impactor 180 and a reverse impaction spring 194 positioned between a second shoulder 154 associated with the impaction shaft 150 and the reverse impactor 190.

As will be described and illustrated herein, the forward and reverse impactors 180, 190 each include a single ramped surface 182, 192. Similarly, each of the first and second ends of the launch cog assembly 160 includes a single ramped surface. The ramped surfaces 164, 166 of the launch cog assembly 160 being arranged and configured to interact with the ramped surfaces 182, 192 formed on the forward and reverse impactors 180, 190 depending on the direction of movement (e.g., forward or reverse). It should be appreciated however that the ramped surfaces 164, 166 of the launch cog assembly 160 and the ramped surfaces 182, 192 of the forward and reverse impactors 180, 190 may include multiple ramped surfaces such as, for example, two, three, or more. Thus arranged, for a given rotation, a higher impact frequency may be provided by the orthopedic impactor 100.

Figure 3:
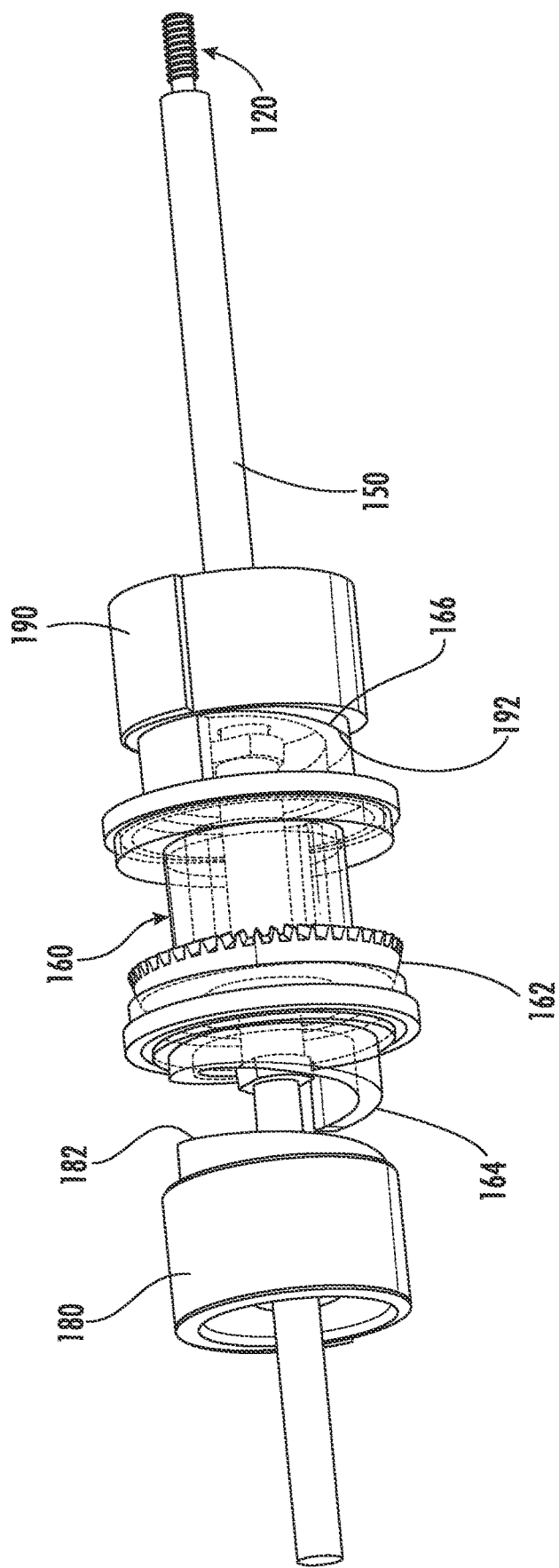
FIG. 3 illustrates a detailed perspective view of some of the internal components of the orthopedic surgical instrument or impactor in accordance with one or more features of the present disclosure, FIG. 3 illustrating an impaction shaft, a launch cog assembly, and forward and reverse impactors.
Figure 4:
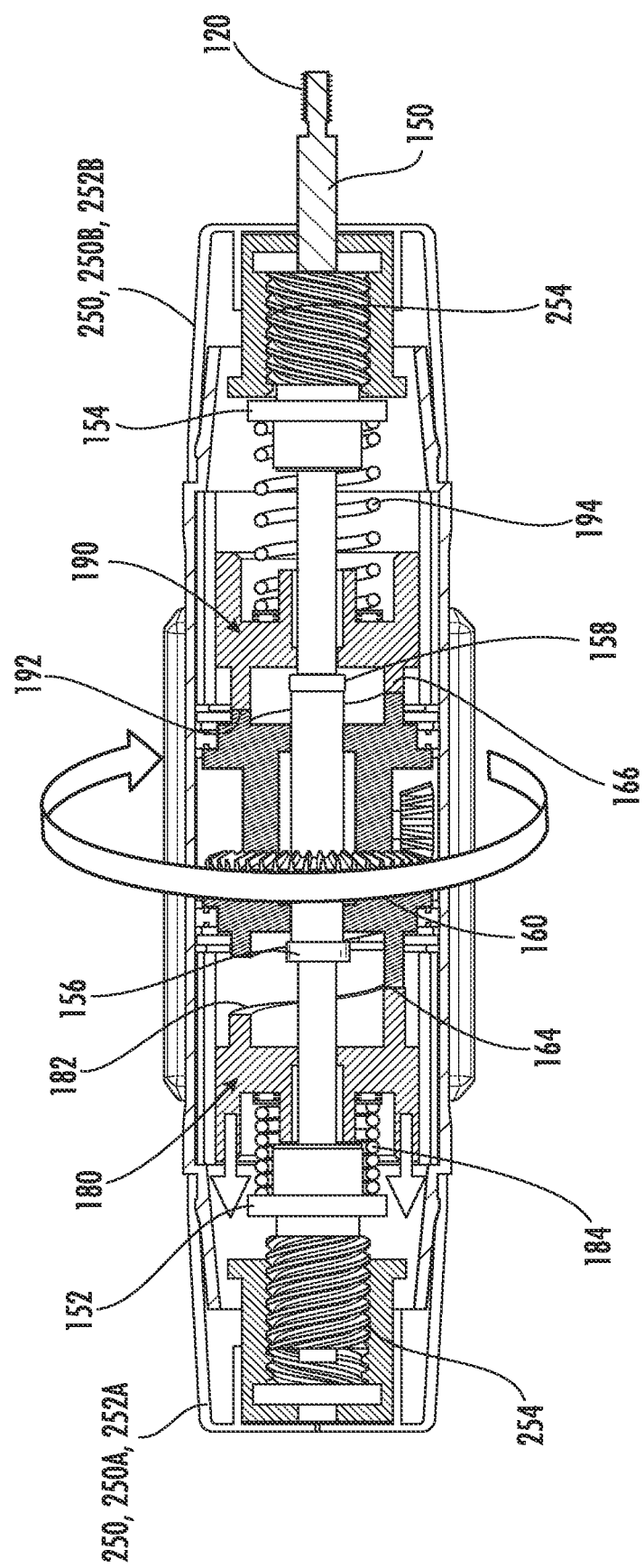
FIG. 4 illustrates a detailed cross-sectional view of the orthopedic surgical instrument or impactor shown in FIG. 1.
Figure 5A:
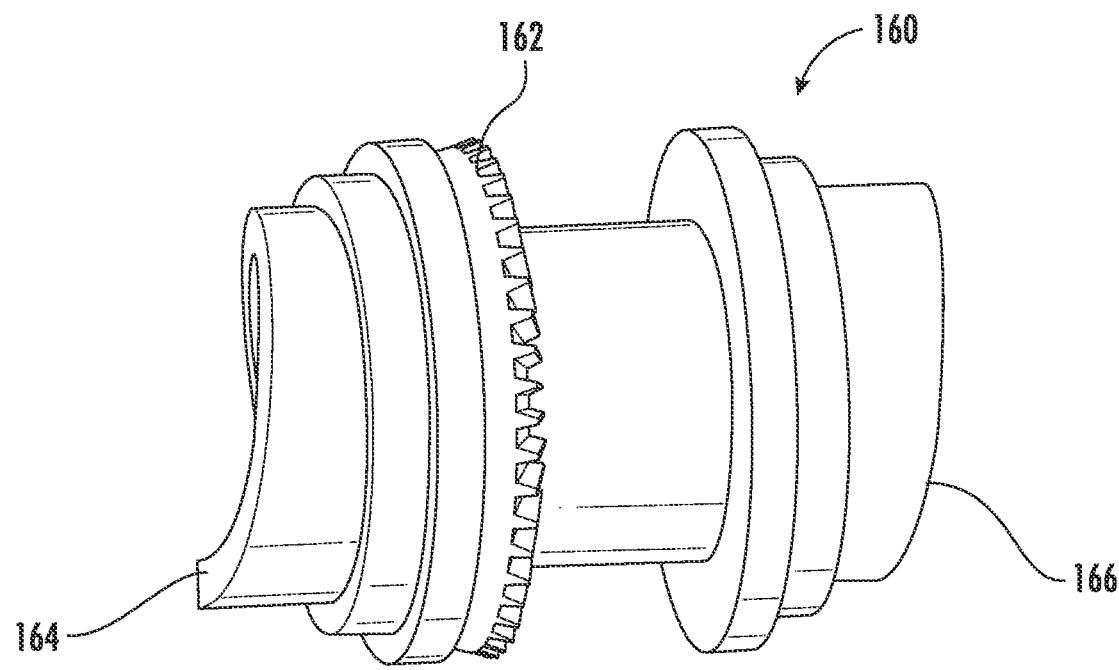
FIG. 5A illustrates a perspective view of an example embodiment of a launch cog assembly in accordance with one or more features of the present disclosure.
Figure 5B:
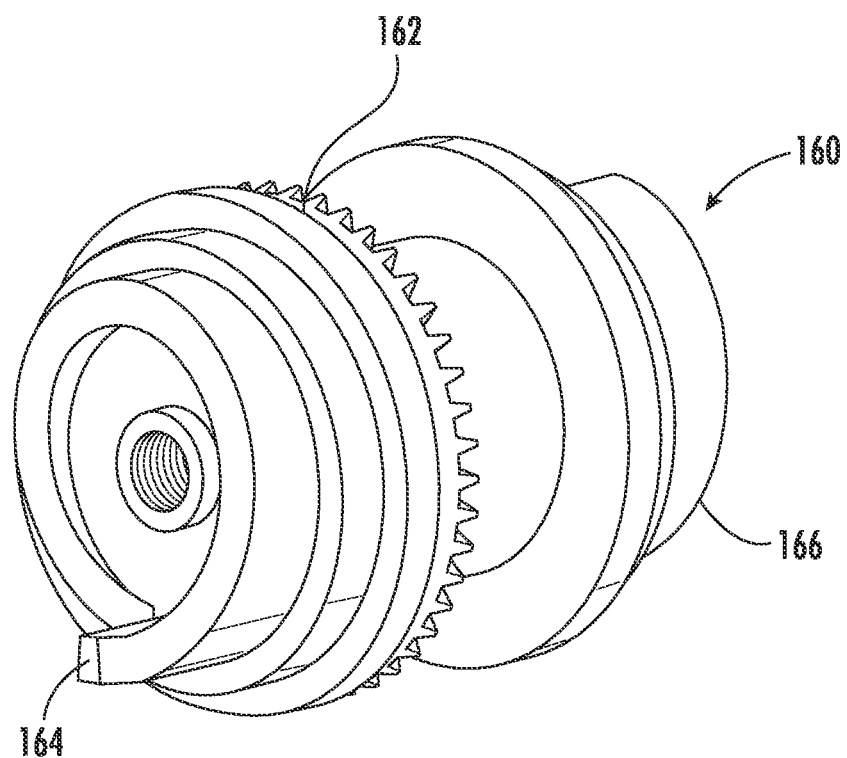
FIG. 5B illustrates an alternate perspective view of the launch cog assembly shown in FIG. 5A.

In use, with the orthopedic impactor 100 positioned in the forward configuration, rotation (e.g., clockwise rotation) of the motor 130 causes the helical gear 162 of the launch cog assembly 160 to rotate in a first direction (e.g., clockwise direction), which in turn, causes the ramped surface 164 of the launch cog assembly 160 to interact with the ramped surface 182 of the forward impactor 180 to move (e.g., translate) the forward impactor 180 relative to the impaction shaft 150 (e.g., rotation of the motor 130 in the forward direction causes the forward impactor 180 to move to the left in FIGS. 2-4). As will be described in greater detail below, with the orthopedic impactor 100 positioned in the forward configuration, the forward impactor 180 remains rotationally stationary. As a result, rotation of the launch cog assembly 160 causes the forward impactor 180 to translate along the impaction shaft 150 and compresses the forward impaction spring 184.

Figure 6:
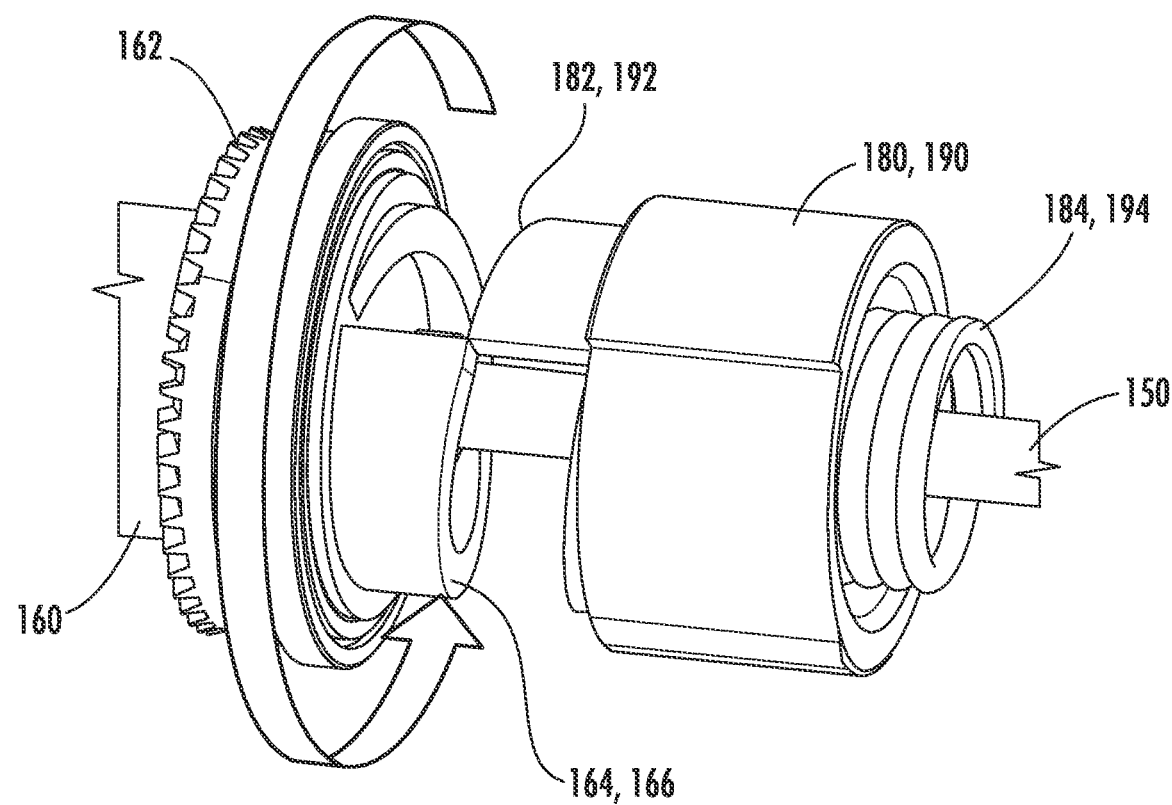
FIG. 6 illustrates a perspective view of the launch cog assembly shown in FIG. 5A interacting with one of the forward and reverse impactors just prior to firing (e.g., a moment before disengagement) in accordance with one or more features of the present disclosure.
Figure 7A:
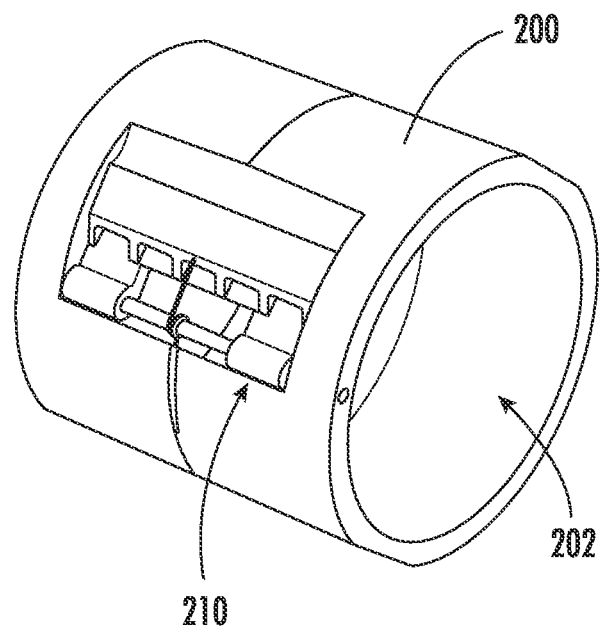
FIG. 7A illustrates a perspective view of an example embodiment of an anti-rotational sleeve assembly in accordance with one or more features of the present disclosure.
Figure 7B:
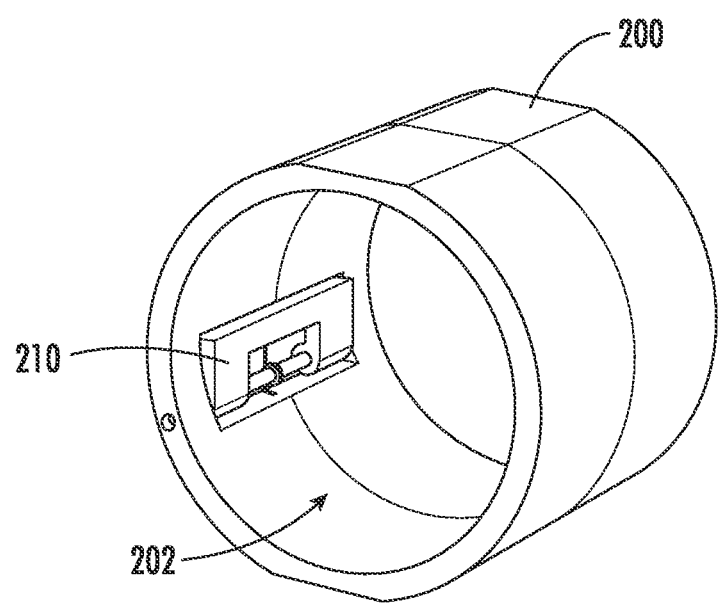
FIG. 7B illustrates an alternate perspective view of the anti-rotational sleeve assembly shown in FIG. 7A.
Figure 7C:
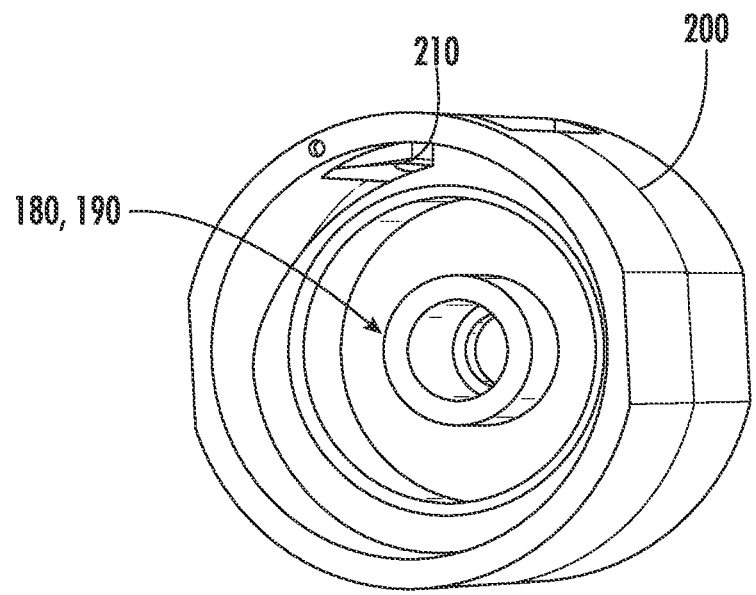
FIG. 7C illustrates a perspective view of the anti-rotational sleeve assembly shown in FIG. 7A along with one of the forward and reverse impactors positioned therein.
Figure 7D:
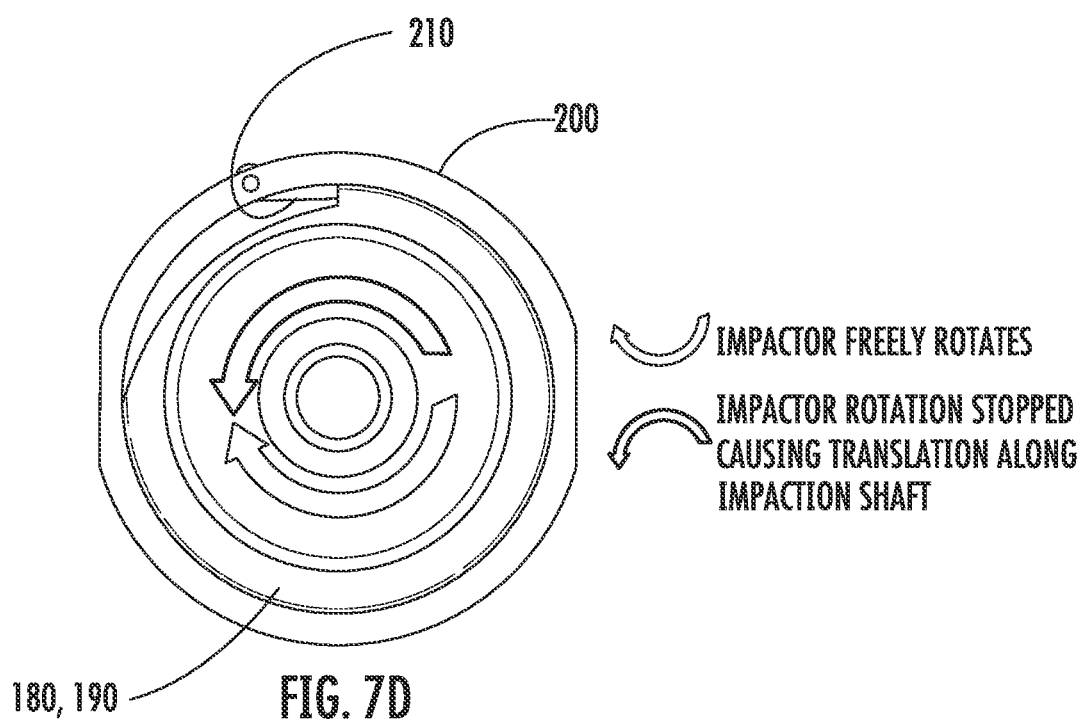
FIG. 7D illustrates a side view of the anti-rotational sleeve assembly and impactor shown in FIG. 7C.

That is, with the forward impactor 180 remaining rotationally stationary, rotation of the launch cog assembly 160 relative to the forward impactor 180 (e.g., to the left in FIGS. 2-4) causes the first or forward ramped surface 164 of the launch cog assembly 160 to interact with the ramped surface 182 of the forward impactor 180. Thereafter continued rotation of the launch cog assembly 160 relative to the impaction shaft 150 causes the first or forward ramped surface 164 of the launch cog assembly 160 to rotate relative to the ramped surface 182 of the forward impactor 180, which in turn causes compression of the forward impaction spring 184 until the first or forward ramped surface 164 of the launch cog assembly 160 disengages from the ramped surface 182 of the forward impactor 180. FIG. 6 illustrates the launch cog assembly 160 and forward impactor 180 just prior to firing (e.g., a moment before disengagement). When the first or forward ramped surface 164 of the launch cog assembly 160 disengages from the ramped surface 182 of the forward impactor 180, the compressed forward impaction spring 184 biases or pushes the forward impactor 180 forward (e.g., to the right in FIGS. 2-4) causing the forward impactor 180 to strike a hammer shoulder 156 positioned on the impaction shaft 150, which drives or transfers the energy to the coupling mechanism 120, and hence to the implant or surgical tool coupled to the orthopedic impactor 100.

As previously mentioned, with the orthopedic impactor 100 positioned in the forward configuration, rotation of the motor 130 is transferred to the launch cog assembly 160 such that the launch cog assembly 160 rotates relative to the impaction shaft 150 thereby, via the interacting ramped surfaces 164, 182, axially translating the forward impactor 180 to compress the forward impaction spring 184 until the forward impactor 180 disengages from the launch cog assembly 160 causing the forward impactor 180 to fire, striking the impaction shaft 150 and driving the orthopedic impactor 100 forward. While this is going on, in the forward configuration, the reverse impactor 190 is unaffected. That is, rotation of the motor 130 is not transferred to the reverse impactor 190 (e.g., rotation of the motor 130 in the forward configuration is not transferred to the reverse impactor 190 so that the reverse impaction spring 194 is not compressed). In the forward configuration, the reverse impactor 190 is freely rotatable in tandem with the launch cog assembly 160 with respect to the impaction shaft 150 (e.g., the reverse impactor 190 and the launch cog assembly 160 rotate in unison, as will be described in greater detail below).

In use, when the orthopedic impactor 100 is transitioned to the reverse configuration so that rotation of the motor 130 drives the launch cog assembly 160 in the opposite direction (e.g., launch cog assembly 160 rotates in a counter-clockwise direction in FIGS. 2-4), the reverse impactor 190 is now transitioned so that the reverse impactor 190 no longer freely rotates in tandem with the launch cog assembly 160. Thus arranged, the second or reverse ramped surface 166 of the launch cog assembly 160 interacts with the ramped surface 192 of the reverse impactor 190 so that continued rotation of the launch cog assembly 160 relative to the impaction shaft 150 causes the second or reverse ramped surface 166 of the launch cog assembly 160 to rotate relative to the ramped surface 192 of the reverse impactor 190, which in turn causes compression of the reverse impaction spring 194 until the second or reverse ramped surface 166 of the launch cog assembly 160 disengages from the ramped surface 192 of the reverse impactor 190. When the second or reverse ramped surface 166 of the launch cog assembly 160 disengages from the ramped surface 192 of the reverse impactor 190, the compressed reversed impaction spring 194 biases or pushes the reverse impactor 190 rearward (e.g., to the left in FIGS. 2-4) causing the reverse impactor 190 to strike a hammer shoulder 158 positioned on the impaction shaft 150, which drives or transfers the energy to the coupling mechanism 120, and hence to the implant or surgical tool coupled to the orthopedic impactor 100.

Referring to FIGS. 2 and 7A-7D, in one embodiment, the orthopedic impactor 100 may include forward and reverse impactor anti-rotational sleeve assemblies 200. In use, for reasons that will become apparent, the forward and reverse impactor anti-rotational sleeve assemblies 200 are stationary (e.g., the forward and reverse impactor anti-rotational sleeve assemblies 200 do not rotate). As illustrated, the anti-rotational sleeve assemblies 200 include a pivoting pawl assembly 210. In use, as illustrated in FIGS. 7A-7D, the anti-rotational sleeve assemblies 200 include an internal bore 202 arranged and configured to receive one of the forward and reverse impactors 180, 190 therein. During use, depending on the direction of rotation, the pawl 210 either engages the impactor 180, 190 thereby preventing relative rotation between the impactor 180, 190 and the anti-rotational sleeve assembly 200 or the pawl 210 pivots away from the impactor 180, 190 thereby allowing the impactor 180, 190 to freely rotate relative to the anti-rotational sleeve assembly 200.

That is, in use, when rotated in a first direction, the impactor 180, 190 is freely rotatable relative to the anti-rotational sleeve assembly 200. However, when rotated in a second direction, opposite the first direction, relative rotation between the impactor 180, 190 and the anti-rotational sleeve assembly 200 is prevented by engagement of the pawl 210 with the impactor 180, 190.

Thus arranged, for example, when the orthopedic impactor 100 is positioned in the forward configuration, the forward impactor 180 rotates in the second direction so that relative rotation between the forward impactor 180 and the forward anti-rotational sleeve assembly 200 is prevented. Meanwhile, the reverse impactor 190 rotates in the first direction so that the reverse impactor 190 is freely rotatable relative to the reverse anti-rotational sleeve assembly 200 so that the reverse impactor 190 rotates with the launch cog assembly 160. As will be readily appreciated, when the orthopedic impactor 100 is positioned in the reverse configuration, the reverse impactor 190 rotates in the second direction and the forward impactor 180 rotates in the first direction.

Figure 8:
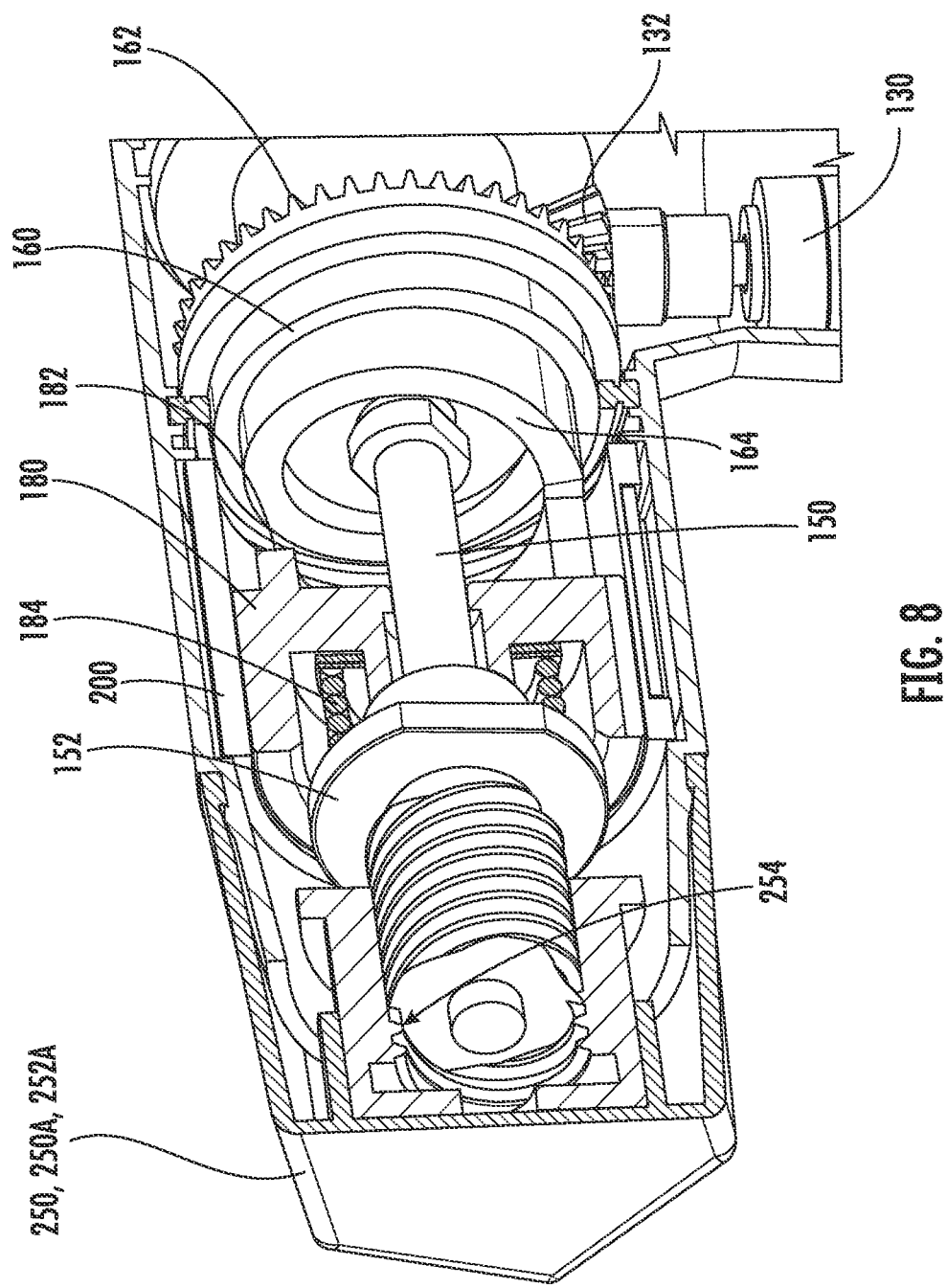
FIG. 8 illustrates a detailed cross-sectional view of an energy adjuster in accordance with one or more features of the present disclosure.

In accordance with one or more features of the present disclosure, referring to FIGS. 1, 2, and 8, the orthopedic impactor 100 may also include an energy adjuster 250 arranged and configured to adjust the energy or impact force provided by the orthopedic impactor 100. In one embodiment, the orthopedic impactor 100 may include a forward energy adjuster 250A and a reverse energy adjuster 250B so that a user can independently adjust the amount of energy provided in the forward direction and in the reverse direction.

In use, the energy adjusters 250 (e.g., the forward energy adjuster 250A and the reverse energy adjuster 250B) may be provided in any suitable form or mechanism now known or hereafter developed. In one embodiment, referring to FIGS. 1, 2, and 8, the orthopedic impactor 100 may include a forward adjuster knob 252A positioned at a rearward side of the orthopedic impactor 100 and a reverse adjuster knob 252B positioned at a forward side of the orthopedic impactor 100. In use, the knobs 252A, 252B may include an internal thread 254 arranged and configured to engage a corresponding thread such as, for example, a multi-start thread, operatively associated with the shoulders 152, 154 of the impaction shaft 150. Incorporation of a multi-start thread reduces the amount of rotational movement needed to adjust between minimum and maximum energy settings. However, it should be appreciated that other forms of threads may be utilized.

In use, rotation of the forward adjuster knob 252A in a first direction compresses the forward impaction spring 184. For example, rotation of the forward adjuster knob 252A causes the forward impaction spring 184 to be compressed between the shoulder 152 and the forward impactor 180. Compression of the forward impaction spring 184, as will be appreciated by one of ordinary skill in the art, increases the preload on the forward impaction spring 184. In use, the greater the preload on the forward impaction spring 184, the greater the impaction force. Meanwhile, in use, rotation of the forward adjuster knob 252A in a second direction, opposite the first direction, relaxes the forward impaction spring 184 thereby decreasing the preload on the forward impaction spring 184. For example, rotation of the forward adjuster knob 252A causes the forward impaction spring 184 to be relaxed thereby decreasing the preload on the forward impaction spring 184.

Similarly, rotation of the reverse adjuster knob 252B in a first direction compresses the reverse impaction spring 194. For example, rotation of the reverse adjuster knob 252B causes the reverse impaction spring 194 to be compressed between the shoulder 154 and the reverse impactor 190. Compression of the reverse impaction spring 194, as will be appreciated by one of ordinary skill in the art, increases the preload on the reverse impaction spring 194. In use, the greater the preload on the reverse impaction spring 194, the greater the retraction force. Meanwhile, in use, rotation of the reverse adjuster knob 252B in a second direction, opposite the first direction, relaxes the reverse impaction spring 194. For example, rotation of the reverse adjuster knob 252B causes the reverse impaction spring 194 to be relaxed thereby decreasing the preload on the reverse impaction spring 194.

Thus arranged, a surgeon is able to independently adjust the preload on the forward and reverse impaction springs 184, 194, and thus independently adjust the force provided by the orthopedic impactor 100 in the forward and reverse directions. This is beneficial as it provides the surgeon with numerous advantages over currently known impactors that do not have impact adjustments and/or independently and separately controlled forward and reverse adjustments. For example, generally speaking, surgeons may prefer to use lower energy or impaction when broaching (e.g., preparing a patient's bone) as compared to when setting an implant. Thus, a surgeon may utilize reduced energy or impaction when broaching and increased energy when setting an implant. In addition, in some embodiments, the orthopedic impactor 100 may also be arranged and configured to provide variable frequency such as, for example, between 1 hz and 16 hz. In use, a surgeon may prefer to utilize increased frequency and lower energy transfer when broaching and lower frequency and increased energy transfer when setting an implant. Alternatively, when broaching, surgeons prefer to drive the broach forward using lower energy or impaction and reverse the broach using higher energy transfer to ensure the broach is freed. In this manner, utilizing the separate and independent controls, the surgeon can drive the broach utilizing a lower preload (e.g., lower energy transfer) in the forward direction while using a higher preload (e.g., greater energy transfer) in the reverse direction.

It should be appreciated that operation of the orthopedic impactor 100 in the forward direction has been described herein with reference to the accompanying figures. As will be appreciated, in use, switching the orthopedic impactor 100 to the reverse configuration, causes the orthopedic impactor 100 to operate in the same manner as the forward configuration except in the opposite direction. That is, with the orthopedic impactor 100 positioned in the reversed configuration, rotation of the motor 130 causes the helical gear 162 of the launch cog assembly 160 to rotate in the opposite (e.g., counter-clockwise) direction, which in turn, causes the launch cog assembly 160 to rotate in the opposite direction relative to the impaction shaft 150. This in turn causes the launch cog assembly 160 to interact with the reverse impactor 190, which causes the reverse impaction spring 194 to compress. Meanwhile, with the orthopedic impactor 100 in the reverse configuration, rotation of the motor 130 is not transferred to the forward impactor 180. Thus, for the sake of brevity of the present disclosure, operation of the orthopedic impactor 100 in the reverse direction will not be described herein.

The foregoing description has broad application. While the present disclosure refers to certain embodiments, numerous modifications, alterations, and changes to the described embodiments are possible without departing from the sphere and scope of the present disclosure, as defined in the appended claim(s). Accordingly, it is intended that the present disclosure not be limited to the described embodiments. Rather these embodiments should be considered as illustrative and not restrictive in character. All changes and modifications that come within the spirit of the invention are to be considered within the scope of the disclosure. The present disclosure should be given the full scope defined by the language of the following claims, and equivalents thereof. The discussion of any embodiment is meant only to be explanatory and is not intended to suggest that the scope of the disclosure, including the claims, is limited to these embodiments. In other words, while illustrative embodiments of the disclosure have been described in detail herein, it is to be understood that the inventive concepts may be otherwise variously embodied and employed, and that the appended claims are intended to be construed to include such variations, except as limited by the prior art. Unless otherwise defined, all technical terms used herein have the same meaning as commonly understood by one of ordinary skill in the art to which the disclosure belongs.

Directional terms such as top, bottom, superior, inferior, medial, lateral, anterior, posterior, proximal, distal, upper, lower, upward, downward, left, right, longitudinal, front, back, above, below, vertical, horizontal, radial, axial, clockwise, and counter-clockwise) and the like may have been used herein. Such directional references are only used for identification purposes to aid the reader's understanding of the present disclosure. For example, the term "distal" may refer to the end farthest away from the medical professional/operator when introducing a device into a patient, while the term "proximal" may refer to the end closest to the medical professional when introducing a device into a patient. Such directional references do not necessarily create limitations, particularly as to the position, orientation, or use of this disclosure. As such, directional references should not be limited to specific coordinate orientations, distances, or sizes, but are used to describe relative positions referencing particular embodiments. Such terms are not generally limiting to the scope of the claims made herein. Any embodiment or feature of any section, portion, or any other component shown or particularly described in relation to various embodiments of similar sections, portions, or components herein may be interchangeably applied to any other similar embodiment or feature shown or described herein.

It should be understood that, as described herein, an "embodiment" (such as illustrated in the accompanying Figures) may refer to an illustrative representation of an environment or article or component in which a disclosed concept or feature may be provided or embodied, or to the representation of a manner in which just the concept or feature may be provided or embodied. However, such illustrated embodiments are to be understood as examples (unless otherwise stated), and other manners of embodying the described concepts or features, such as may be understood by one of ordinary skill in the art upon learning the concepts or features from the present disclosure, are within the scope of the disclosure. Furthermore, references to "one embodiment" of the present disclosure are not intended to be interpreted as excluding the existence of additional embodiments that also incorporate the recited features.

In addition, it will be appreciated that while the Figures may show one or more embodiments of concepts or features together in a single embodiment of an environment, article, or component incorporating such concepts or features, such concepts or features are to be understood (unless otherwise specified) as independent of and separate from one another and are shown together for the sake of convenience and without intent to limit to being present or used together. For instance, features illustrated or described as part of one embodiment can be used separately, or with another embodiment to yield a still further embodiment. Thus, it is intended that the present subject matter covers such modifications and variations as come within the scope of the appended claims and their equivalents.

As used herein, an element or step recited in the singular and proceeded with the word "a" or "an" should be understood as not excluding plural elements or steps, unless such exclusion is explicitly recited. It will be further understood that the terms "comprises" and/or "comprising," or "includes" and/or "including" when used herein, specify the presence of stated features, regions, steps, elements and/or components, but do not preclude the presence or addition of one or more other features, regions, integers, steps, operations, elements, components and/or groups thereof.

The phrases "at least one", "one or more", and "and/or", as used herein, are open-ended expressions that are both conjunctive and disjunctive in operation. The terms "a" (or "an"), "one or more" and "at least one" can be used interchangeably herein.

Connection references (e.g., engaged, attached, coupled, connected, and joined) are to be construed broadly and may include intermediate members between a collection of elements and relative to movement between elements unless otherwise indicated. As such, connection references do not necessarily infer that two elements are directly connected and in fixed relation to each other. Identification references (e.g., primary, secondary, first, second, third, fourth, etc.) are not intended to connote importance or priority, but are used to distinguish one feature from another. The drawings are for purposes of illustration only and the dimensions, positions, order and relative to sizes reflected in the drawings attached hereto may vary.

The foregoing discussion has been presented for purposes of illustration and description and is not intended to limit the disclosure to the form or forms disclosed herein. For example, various features of the disclosure are grouped together in one or more embodiments or configurations for the purpose of streamlining the disclosure. However, it should be understood that various features of the certain embodiments or configurations of the disclosure may be combined in alternate embodiments or configurations. Moreover, the following claims are hereby incorporated into this Detailed Description by this reference, with each claim standing on its own as a separate embodiment of the present disclosure.

We claim:

1. An orthopedic surgical instrument arranged and configured to deliver a first forward motion to drive a surgical tool or implant into a patient's bone and a second reverse motion to remove a surgical tool or implant from the patient's bone, the surgical instrument comprising:
    a housing;
    a motor positioned within the housing, the motor including a first gear;
    a launch cog assembly including a second gear arranged and configured to interact with the first gear of the motor so that activation of the motor rotates the launch cog assembly in one of a first direction or a second direction, the log cog assembly including a first end and a second end;
    a forward impactor arranged and configured to interact with the first end of the launch cog assembly; and
    a reverse impactor arranged and configured to interact with the second end of the launch cog assembly;
    wherein, in use, with the orthopedic surgical instrument in a forward configuration, activation of the motor rotates the launch cog assembly in the first direction causing the first end of the launch cog assembly to interact with the forward impactor to axially translate the forward impactor;
    wherein, in use, with the orthopedic surgical instrument in a reverse configuration, activation of the motor rotates the launch cog assembly in the second direction causing the second end of the launch cog assembly to interact with the reverse impactor to axially translate the reverse impactor; and
    wherein the first end of the launch cog assembly includes a first ramped surface, the second end of the launch cog assembly includes a second ramped surface, the forward impactor includes a ramped surface arranged and configured to interact with the first ramped surface of the launch cog assembly, and the reverse impactor includes a ramped surface arranged and configured to interact with the second ramped surface of the launch cog assembly.

2. The orthopedic surgical instrument according to claim 1, further comprising a shaft, the launch cog assembly, the forward impactor, and the reverse impactor being mounted about the shaft.

3. The orthopedic surgical instrument according to claim 2, further comprising:

a first spring positioned about the shaft, the first spring positioned between the forward impactor and a first shoulder of the shaft; and a second spring positioned about the shaft, the second spring positioned between the reverse impactor and a second shoulder of the shaft.

4. The orthopedic surgical instrument according to claim 3, wherein with the orthopedic surgical instrument in the forward configuration, interaction between the first ramped surface on the first end of the launch cog assembly and the ramped surface on the forward impactor causes the first spring to compress until the first ramped surface on the first end of the launch cog assembly and the ramped surface on the forward impactor disengage causing the first spring to axially drive the forward impactor relative to the shaft.

5. The orthopedic surgical instrument according to claim 4, wherein with the orthopedic surgical instrument in the reverse configuration, interaction between the second ramped surface on the second end of the launch cog assembly and the ramped surface on the reverse impactor causes the second spring to compress until the second ramped surface on the second end of the launch cog assembly and the ramped surface on the reverse impactor disengage causing the second spring to axially drive the reverse impactor relative to the shaft.

6. The orthopedic surgical instrument according to claim 2, wherein with the orthopedic surgical instrument in the forward configuration, the forward impactor is rotationally stationary relative to the shaft.

7. The orthopedic surgical instrument according to claim 6, wherein with the orthopedic surgical instrument in the forward configuration, the reverse impactor is rotatable relative to the shaft so that the reverse impactor rotates with the launch cog assembly.

8. The orthopedic surgical instrument according to claim 7, wherein with the orthopedic surgical instrument in the reverse configuration, the reverse impactor is rotationally stationary relative to the shaft, and the forward impactor is rotatable relative to the shaft so that the forward impactor rotates with the launch cog assembly.

9. The orthopedic surgical instrument according to claim 6, further comprising:
a forward impactor anti-rotational sleeve including an internal bore arranged and configured to receive the forward impactor therein and a pawl arranged and configured to selectively engage the forward impactor depending on a direction of rotation, engagement of the pawl with the forward impactor prevents relative rotation of the forward impactor; and
a reverse impactor anti-rotational sleeve including an internal bore arranged and configured to receive the reverse impactor therein and a pawl arranged and configured to selectively engage the reverse impactor depending on the direction of rotation, engagement of the pawl with the reverse impactor prevents relative rotation of the reverse impactor.

10. The orthopedic surgical instrument according to claim 3, further comprising:
a forward energy adjuster and a reverse energy adjuster arranged and configured to enable a user to independently adjust an amount of energy provided in the forward configuration and in the reverse configuration.

11. The orthopedic surgical instrument according to claim 10, wherein:
the forward energy adjuster includes a first knob including an internal thread arranged and configured to engage a corresponding thread operatively associated with the first shoulder of the shaft, in use, rotation of the first knob in a first direction compresses the first spring to increase a preload on the first spring, rotation of the first knob in a second direction relaxes the first spring to decrease the preload on the first spring; and
the reverse energy adjuster includes a second knob including an internal thread arranged and configured to engage a corresponding thread operatively associated with the second shoulder of the shaft, in use, rotation of the second knob in a first direction compresses the second spring to increase a preload on the second spring, rotation of the second knob in a second direction relaxes the second spring to decrease the preload on the second spring.

12. The orthopedic surgical instrument according to claim 1, further comprising a selector mechanism arranged and configured to transition the orthopedic surgical instrument between forward configuration and the reverse configuration.

13. The orthopedic surgical instrument according to claim 1, further comprising a coupling mechanism operatively associated with the shaft, the coupling mechanism arranged and configured to couple to a surgical tool or an implant.

14. An orthopedic surgical instrument arranged and configured to deliver a first forward motion to drive a surgical tool or implant into a patient's bone and a second reverse motion to remove a surgical tool or implant from the patient's bone, the surgical instrument comprising:
a housing;
a motor positioned within the housing, the motor including a first gear;
a launch cog assembly including a second gear arranged and configured to interact with the first gear of the motor so that activation of the motor rotates the launch cog assembly in one of a first direction or a second direction, the log cog assembly including a first end and a second end;
a forward impactor arranged and configured to interact with the first end of the launch cog assembly;
a reverse impactor arranged and configured to interact with the second end of the launch cog assembly;
wherein the orthopedic surgical instrument is operable in a forward configuration so that activation of the motor rotates the launch cog assembly in the first direction and in a reverse configuration so that activation of the motor rotates the launch cog assembly in the second direction;
wherein the orthopedic surgical instrument further includes a forward energy adjuster and a reverse energy adjuster arranged and configured to enable a user to independently adjust an amount of energy provided in the forward configuration and in the reverse configuration; and
wherein the surgical instrument further comprises a shaft, the launch cog assembly, the forward impactor, and the reverse impactor being mounted about the shaft;
a first spring positioned about the shaft, the first spring positioned between the forward impactor and a first shoulder of the shaft; and
a second spring positioned about the shaft, the second spring positioned between the reverse impactor and a second shoulder of the shaft.

15. The orthopedic surgical instrument according to claim 14, wherein:
the forward energy adjuster includes a first knob including an internal thread arranged and configured to engage a corresponding thread operatively associated with the first shoulder of the shaft, in use, rotation of the first knob in a first direction compresses the first spring to increase a preload on the first spring, rotation of the first knob in a second direction relaxes the first spring to decrease the preload on the first spring; and the reverse energy adjuster includes a second knob including an internal thread arranged and configured to engage a corresponding thread operatively associated with the second shoulder of the shaft, in use, rotation of the second knob in a first direction compresses the second spring to increase a preload on the second spring, rotation of the second knob in a second direction relaxes the second spring to decrease the preload on the second spring.

16. The orthopedic surgical instrument according to claim 14, wherein:

in use, with the orthopedic surgical instrument in the forward configuration, activation of the motor rotates the launch cog assembly in the first direction causing the first end of the launch cog assembly to interact with the forward impactor to axially translate the forward impactor; and with the orthopedic surgical instrument in the reverse configuration, activation of the motor rotates the launch cog assembly in the second direction causing the second end of the launch cog assembly to interact with the reverse impactor to axially translate the reverse impactor.

17. The orthopedic surgical instrument according to claim 16, wherein the first end of the launch cog assembly includes a first ramped surface, the second end of the launch cog assembly includes a second ramped surface, the forward impactor includes a ramped surface arranged and configured to interact with the first ramped surface of the launch cog assembly, and the reverse impactor includes a ramped surface arranged and configured to interact with the second ramped surface of the launch cog assembly.

18. The orthopedic surgical instrument according to claim 17, wherein with the orthopedic surgical instrument in the forward configuration, interaction between the first ramped surface on the first end of the launch cog assembly and the ramped surface on the forward impactor causes the first spring to compress until the first ramped surface on the first end of the launch cog assembly and the ramped surface on the forward impactor disengage causing the first spring to axially drive the forward impactor relative to the shaft.

19. The orthopedic surgical instrument according to claim 18, wherein with the orthopedic surgical instrument in the reverse configuration, interaction between the second ramped surface on the second end of the launch cog assembly and the ramped surface on the reverse impactor causes the second spring to compress until the second ramped surface on the second end of the launch cog assembly and the ramped surface on the reverse impactor disengage causing the second spring to axially drive the reverse impactor relative to the shaft.

* * * * *